(12) United States Patent
Haggstrom et al.

(10) Patent No.: US 9,789,278 B2
(45) Date of Patent: Oct. 17, 2017

(54) CATHETER ASSEMBLY WITH REPLACEABLE COMPONENTS

(71) Applicant: Covidien LP, Mansfield, MA (US)

(72) Inventors: Kurt Haggstrom, Huntington Beach, CA (US); Robert Frechette, Lafayette, CO (US)

(73) Assignee: Covidien LP, Mansfield, MA (US)

( * ) Notice: Subject to any disclaimer, the term of this patent is extended or adjusted under 35 U.S.C. 154(b) by 918 days.

(21) Appl. No.: 13/623,418

(22) Filed: Sep. 20, 2012

(65) Prior Publication Data

US 2014/0081245 A1    Mar. 20, 2014

(51) Int. Cl.
*A61M 25/00*    (2006.01)
*A61M 39/10*    (2006.01)

(52) U.S. Cl.
CPC .... *A61M 25/0026* (2013.01); *A61M 25/0028* (2013.01); *A61M 25/0097* (2013.01); *A61M 39/105* (2013.01)

(58) Field of Classification Search
CPC .......... A61M 25/0026; A61M 25/0028; A61M 25/0097; A61M 25/02; A61M 39/105; A61M 39/10
USPC .... 604/43, 165.01, 523, 533, 534, 535, 536, 604/538, 540; 285/124.1, 124.2, 124.4, 285/152.1; 403/219, 296, 299
See application file for complete search history.

(56) References Cited

U.S. PATENT DOCUMENTS

| | | |
|---|---|---|
| 4,419,094 A | 12/1983 | Patel |
| 4,682,978 A | 7/1987 | Martin |
| 4,850,350 A | 7/1989 | Jackson |
| 5,178,423 A | 1/1993 | Combeau |
| 5,741,084 A | 4/1998 | Del Rio et al. |
| 6,638,242 B2 * | 10/2003 | Wilson ................ A61M 1/3653 604/43 |

(Continued)

FOREIGN PATENT DOCUMENTS

| | | |
|---|---|---|
| CA | 1219785 A1 | 3/1987 |
| CN | 1498125 A | 5/2004 |

(Continued)

OTHER PUBLICATIONS

European Search Report from EP Application No. 13181184 dated Nov. 19, 2013.

(Continued)

*Primary Examiner* — Theodore Stigell
*Assistant Examiner* — Amber Stiles
(74) *Attorney, Agent, or Firm* — Kenneth Collier; Jessica Kwak Rauckman

(57) ABSTRACT

A catheter assembly includes a catheter, a collar, and an extension tube assembly. The catheter includes a leading end portion and a trailing end portion. The collar is supported on the trailing end portion of the catheter. The extension tube assembly includes a first section and a second section, each section independent of the other section and including a substantially rigid body portion and a compressible extension tube portion. The body portion of each of the first and second sections is independently engageable with the trailing end portion of the catheter. The collar is configured to engage the first and second sections of the extension tube assembly to secure the extension tube assembly to the trailing end portion of the catheter.

18 Claims, 5 Drawing Sheets

(56) References Cited

U.S. PATENT DOCUMENTS

| | | | |
|---|---|---|---|
| 6,971,390 B1 | 12/2005 | Vasek et al. | |
| 7,152,885 B2 * | 12/2006 | Takamatsu et al. | 285/124.1 |
| 7,341,284 B2 | 3/2008 | Mittersteiner et al. | |
| 7,527,300 B2 | 5/2009 | Li | |
| 7,594,910 B2 | 9/2009 | Butts et al. | |
| 7,601,147 B2 | 10/2009 | Waller et al. | |
| 7,981,093 B2 * | 7/2011 | Schon et al. | 604/284 |
| 2003/0097091 A1 * | 5/2003 | Hobbs et al. | 604/43 |
| 2004/0059314 A1 | 3/2004 | Schon et al. | |
| 2004/0171997 A1 | 9/2004 | Wilson et al. | |
| 2005/0161943 A1 | 7/2005 | Takamatsu et al. | |
| 2005/0267400 A1 | 12/2005 | Haarala et al. | |
| 2006/0108792 A1 | 5/2006 | Takasaki et al. | |
| 2008/0097386 A1 | 4/2008 | Osypka | |
| 2008/0214991 A1 | 9/2008 | Haarala et al. | |
| 2008/0312640 A1 | 12/2008 | Grant | |
| 2009/0088699 A1 | 4/2009 | King et al. | |
| 2011/0098679 A1 * | 4/2011 | Barron et al. | 604/533 |

FOREIGN PATENT DOCUMENTS

| | | |
|---|---|---|
| JP | 2004526481 A | 9/2004 |
| JP | 2007330688 A | 12/2007 |
| JP | 2009504338 A | 2/2009 |
| WO | 2004020019 A2 | 3/2004 |
| WO | 2007137545 A1 | 12/2007 |

OTHER PUBLICATIONS

Notification of the First Office Action, and translation thereof, from counterpart Chinese Patent Application No. 201310426178.8, dated Jan. 26, 2015, 16 pp.

Examination Report from counterpart Canadian Patent Application No. 2824273, dated Aug. 21, 2014, 2 pp.

Notice of Reasons for Rejection, and translation thereof, from counterpart Japanese Patent Application No. 2013191747, dated Oct. 16, 2014, 8 pp.

Second Office Action, and translation thereof, from counterpart Chinese Application No. 201310426178.8, dated Sep. 24, 2015, 10 pp.

Notification of Reason for Rejection, and translation thereof, from counterpart Japanese Patent Application No. 2013-191747, dated Jul. 7, 2016, 5 pp.

Third Office Action, and translation thereof, from counterpart Chinese Patent Application No. 201310426178.8, dated Mar. 15, 2016, 18 pp.

Notice of Final Rejection, and translation thereof, from counterpart Japanese Patent Application No. 2013-191747, mailed Aug. 4, 2015, 8 pp.

* cited by examiner

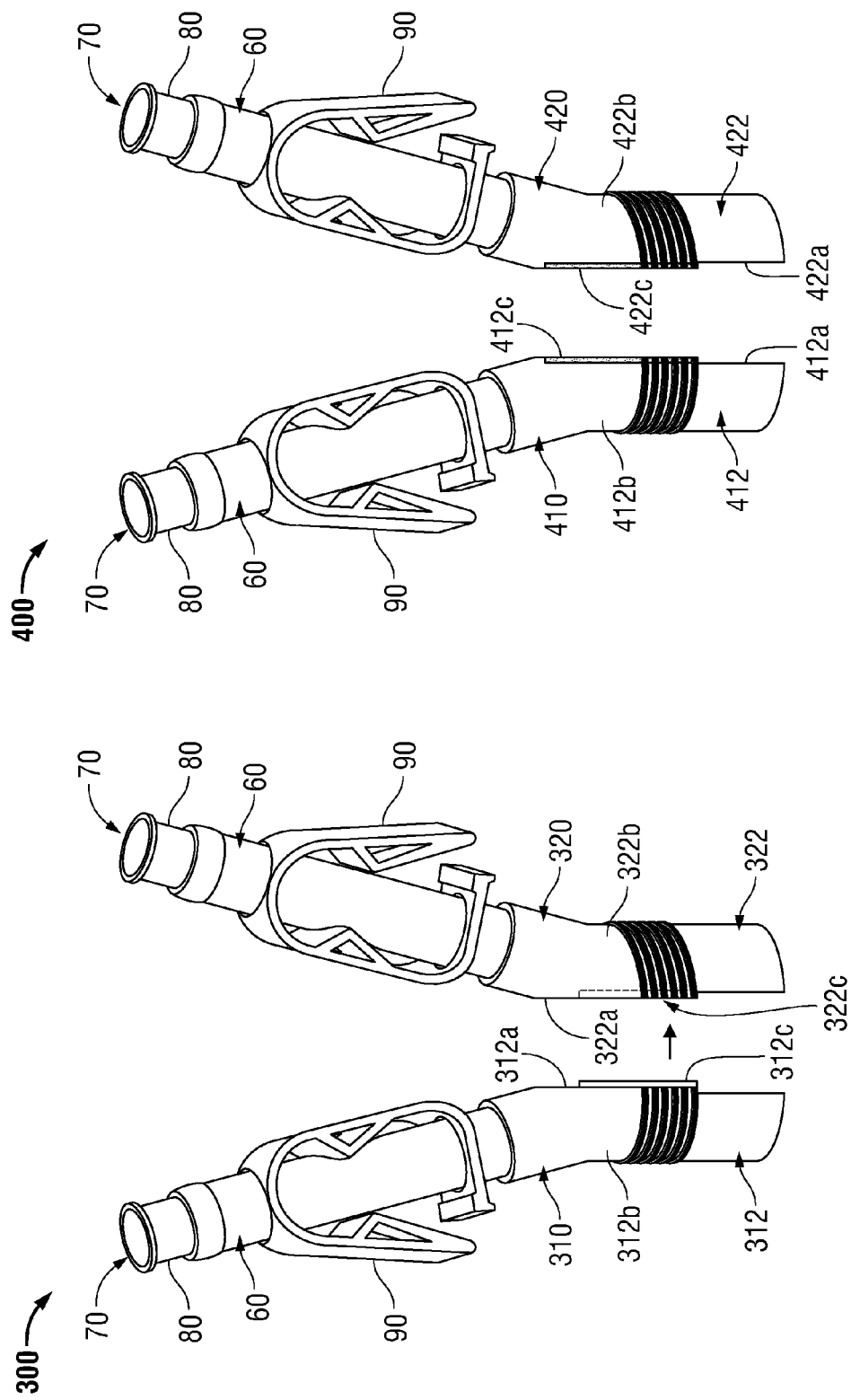

CATHETER ASSEMBLY WITH REPLACEABLE COMPONENTS

TECHNICAL FIELD

The present disclosure generally relates to catheter assemblies, and more particularly, to a catheter assembly with replaceable components.

BACKGROUND

Catheters are flexible medical instruments which facilitate the withdrawal and introduction of fluids from and to body cavities, ducts, and vessels. Catheters may have particular application in a hemodialysis procedure where blood is withdrawn from a blood vessel for treatment, and subsequently returned to the blood vessel for circulation. Known hemodialysis catheter assemblies include multiple lumen catheters, such as dual lumen or triple-lumen catheters, which permit bi-directional fluid flow within the catheter, with one lumen dedicated for withdrawal of blood from a vessel and the other lumen dedicated for return of treated blood to the vessel. During an exemplary hemodialysis procedure, a multiple lumen catheter is inserted into a body and blood is withdrawn through an arterial lumen of the catheter. The removed blood is directed, via extension tubes, to a hemodialysis machine which dialyzes, or purifies, the blood to remove waste and toxins.

Typically, an extension tube assembly is connected to a proximal end of the multilumen catheter and is adapted to communicate with a medical device such as a hemodialysis machine. The extension tube assembly includes a first extension tube for communicating an arterial lumen of a catheter to a hemodialysis machine and a second extension tube for communicating a venous lumen of a catheter with the hemodialysis machine.

Multilumen catheters for dialysis treatment are placed within a patient for use over extended periods of time. During such use, the extension tubes can wear, requiring replacement of the dialysis catheter and/or the extension tube assembly.

SUMMARY

In general, according to one aspect of the present disclosure, a catheter assembly includes a catheter, a collar, and an extension tube assembly. The catheter includes a leading end portion and a trailing end portion. The collar is supported on the trailing end portion of the catheter. The catheter defines a first lumen and a second lumen.

The extension tube assembly includes a first section and a second section, each section being independent of the other section and each section including a substantially rigid body portion and a compressible extension tube portion. The body portion of each of the first and second sections is independently engageable with the trailing end portion of the catheter, and the collar is engageable with the first and second sections of the extension tube assembly to secure the extension tube assembly to the trailing end portion of the catheter. When the body portions of the first and second sections of the extension tube assembly are engaged with the trailing end portion of the catheter, the first lumen of the catheter is in fluid communication with the extension tube portion of the first section of the extension tube assembly and the second lumen of the catheter is in fluid communication with the extension tube portion of the second section of the extension tube assembly.

The collar, which is threaded, is rotatably disposed about the trailing end portion of the catheter relative to the extension tube assembly for threaded engagement of the collar with the body portions of the first and second sections of the extension tube assembly to secure the extension tube assembly to the trailing end portion of the catheter.

The body portions of the first and second sections of the extension tube assembly each include a planar surface. Each planar surface is disposed opposite the planar surface of the other section when the body portions of the first and second sections are engaged with the tailing end portion of the catheter. The body portion of the first section includes a first threaded segment and the body portion of the second section includes a second threaded segment. Each of the first and second threaded segments is threadably engageable with the collar. When the body portions of the first and second sections of the extension tube assembly are disposed adjacent each other, the first threaded segment of the body portion of the first section and the second threaded segment of the body portion of the second section may be simultaneously threadably engageable with the collar. The first threaded segment of the body portion of the first section and the second threaded segment of the body portion of the second section together define an annular threaded arrangement circumscribing the body portions of the first and second sections. The first threaded segment and the second threaded segment of the respective body portions of the first and second sections define the annular threaded arrangement when the first and second threaded segments are axially aligned along a longitudinal axis defined through the extension tube assembly.

One or both of the first and second sections of the extension tube assembly may include a mating feature that axially aligns the first section with the second section. The mating feature may include one or more of an adhesive material, a magnetic material, or combinations thereof. The first section may have a first mating feature including one or more slots defined in the first body portion and the second section may have a second mating feature including one or more detents extending from the second body portion. The one or more detents are positionable within the one or more slots to align the first threaded segment of the body portion of the first section with the second threaded segment of the body portion of the second section.

In general, according to another aspect of the present disclosure, an extension tube assembly for attachment to a catheter includes a first section and a second section. The first section includes a first body portion and a first extension tube portion. The first body portion is securable to a trailing end portion of a catheter and the first extension tube portion is securable to a medical device. The second section includes a second body portion and a second extension tube portion. The second body portion is securable, independently of the first body portion, to the trailing end portion of the catheter and the second extension tube portion is securable to the medical device. The second section is separate and distinct from the first section.

The first body portion and the second body portion each include a planar surface. Each planar surface is disposed opposite the other planar surface when the first and second body portions are engaged with the trailing end of the catheter. The first body portion of the first section includes a first threaded segment and the second body portion of the second section includes a second threaded segment. The first and second body portions together define an annular threaded arrangement when the first and second threaded segments are disposed adjacent each other. The annular threaded arrangement of the first and second body portions is threadably engageable with a collar supported on the catheter for simultaneously securing the first and second body portions to the catheter.

One or both of the first and second sections includes a mating feature that axially aligns the first section with the second section. The mating feature may include one or more of an adhesive material, a magnetic material, or combinations thereof. The first section may have a first mating feature including one or more slots defined in the first body portion and the second section may have a second mating feature including one or more detents extending from the second body portion. One or more detents are positionable within the one or more slots to axial align the first body portion with the second body portion.

Embodiments can include one or more of the following advantages.

In some embodiments, each body portion of the first and second sections of the extension tube assembly is independently engageable with the trailing end portion of the catheter. Such independent engagement of the first and second sections of the extension tube assembly to the trailing end portion of the catheter can facilitate replacement of all or a portion of the extension tube assembly. For example, the first and/or second sections of the extension tube assembly can be replaced without requiring replacement of the entire extension tube assembly and/or replacement of the entire catheter assembly.

In certain embodiments, the collar, supported on the catheter, is engageable with the first and second sections of the extension tube assembly to secure the extension tube assembly to the trailing end portion of the catheter. Such engagement of the collar to the first and second sections of the extension tube assembly can additionally or alternatively facilitate replacement of all or a portion of the extension tube assembly. For example, the engagement and disengagement of the collar with the first and second sections can facilitate removal of one or both of the first and second sections of the extension tube assembly without requiring replacement of the entire extension tube assembly and/or replacement of the entire catheter assembly.

Other aspects, features, and advantages will be apparent from the description drawings and from the claims.

DESCRIPTION OF DRAWINGS

FIG. 4 is a front perspective view of an extension tube assembly of a catheter assembly.

FIG. 5 is a front perspective view of an extension tube assembly of a catheter assembly.

DETAILED DESCRIPTION

As used herein, the terms "proximal" or "trailing" refer to the portion of a structure that is closer to a clinician, while the terms "distal" or "leading" refer to the portion of a structure that is farther from the clinician. As used herein, the term "subject" refers to a human patient or other animal. The term "clinician" refers to a doctor, nurse or other care provider and may include support personnel.

Figure 1:
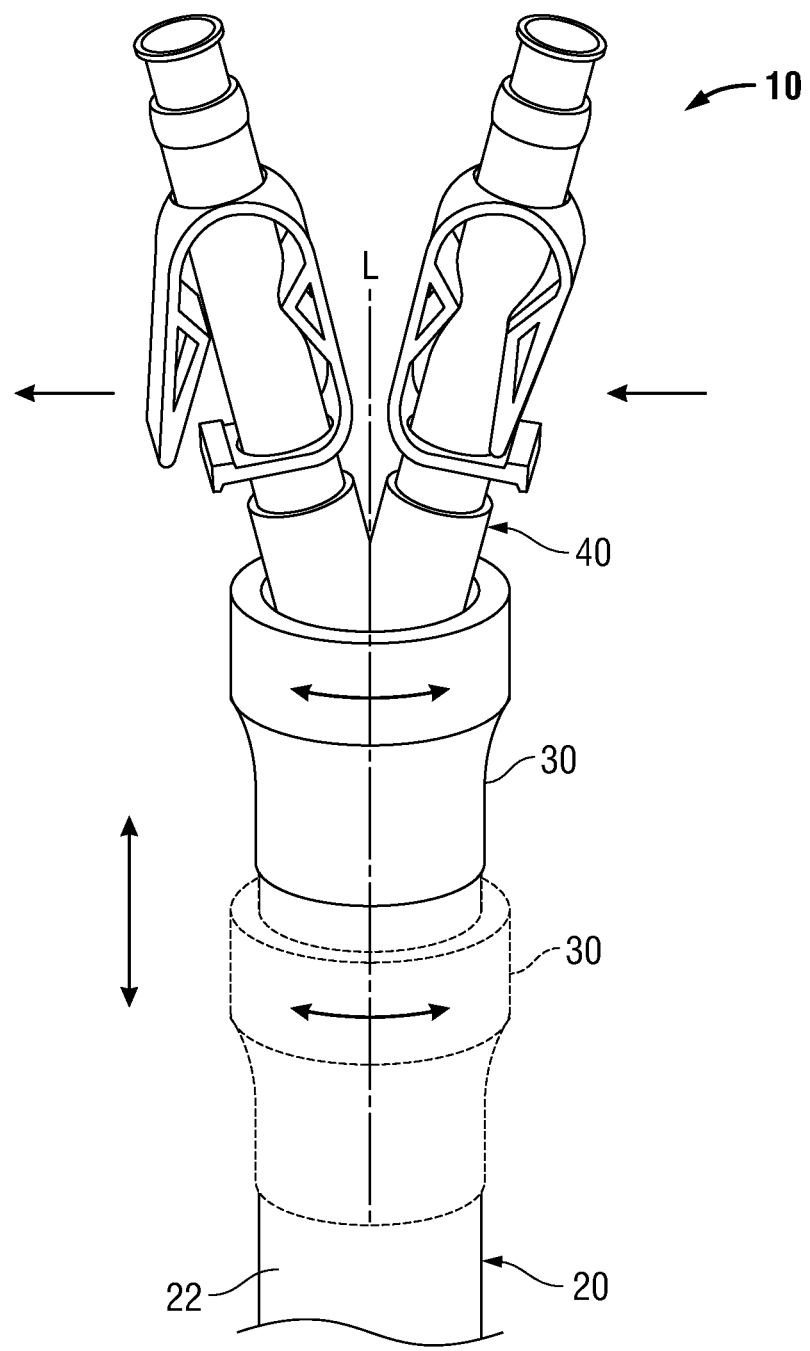
FIG. 1 is a front perspective view of a catheter assembly.
Figure 2:
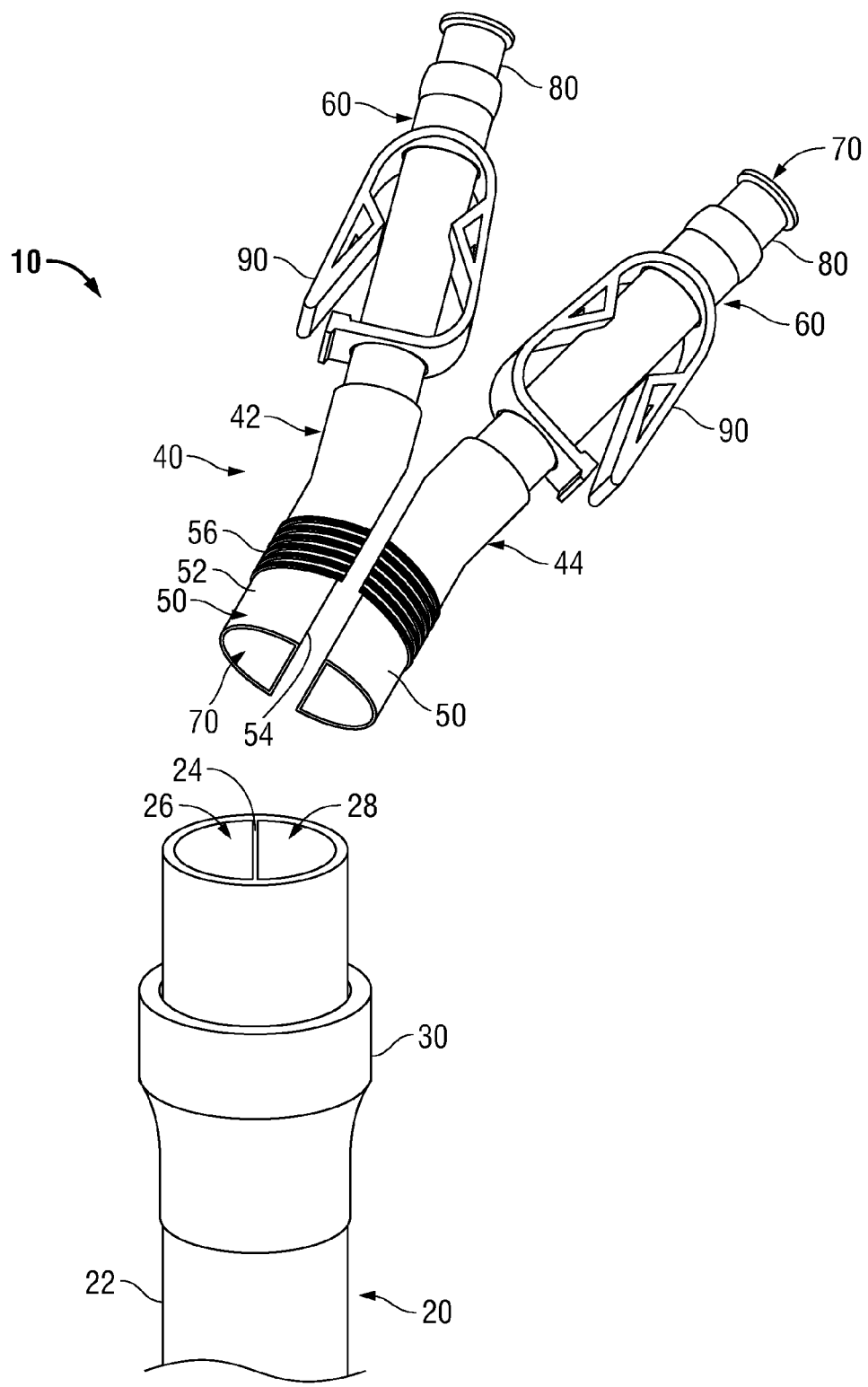
FIG. 2 is a front perspective view, with parts separated, of the catheter assembly of FIG. 1.
Figure 3:
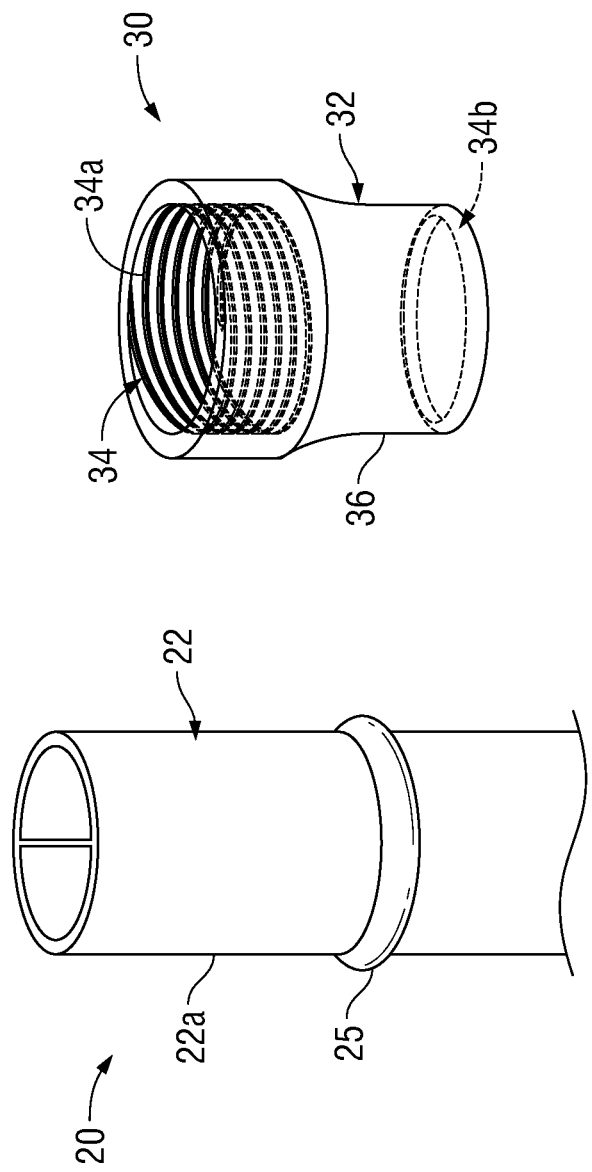
FIG. 3 is a front perspective view of a distal end portion of a catheter and a collar of the catheter assembly of FIG. 1.

Referring now to FIGS. 1-3, a catheter assembly 10 includes a catheter 20, a collar 30, and an extension tube assembly 40. The catheter 20 includes an elongated body 22 having a septum 24 that extends the length of the elongated body 22 to define a first lumen 26 and a second lumen 28 on opposed sides of the septum 24. The first and second lumens 26, 28 may have substantially D-shaped cross-sections, as shown in FIG. 2. Additionally or alternatively, the first and second lumens 26, 28 may have other cross-sections, such as circular, oval, polygonal, etc. The elongated body 22 defines a longitudinal axis "L" extending between trailing and leading ends of the elongated body 22. The elongated body 22 of the catheter 20 may include an annulus 25 disposed on an outer surface 22a of the elongated body 22, as described in further detail below.

The collar 30 is supported on the proximal portion of the elongated body 22 of the catheter 20. The collar 30 includes a collar body 32 having an internal surface 34 and an external surface 36. The internal surface 34 includes a threaded portion 34a at one end of the collar 30 and a lip portion 34b at the other end of the collar 30. The lip portion 34b is engageable with the annulus 25 of the catheter 20 to reduce the likelihood that the collar 30 will slide over or off of the proximal end portion of the catheter 20. The collar 30 is axially translatable relative to the catheter 20. In a proximal-most position of the collar 30 relative to the catheter 20, the lip portion 34b of the collar 30 engages the annulus 25 of the catheter 20 to limit further proximal movement of the collar 30 in relation to the catheter 30 while permitting rotational movement of the collar 30 about the outer surface 22a of the catheter 20.

The extension tube assembly 40 includes a first section 42 and a second section 44, the first section 42 and the second section 44 being substantially identical to one another. Each section 42, 44 includes a body portion 50 and an extension tube portion 60 that together define a respective lumen 70. The body portion 50 can be formed of a substantially rigid material, for example, any hard polymeric material, and the extension tube portion 60 can be formed of a compressible material such as silicone or any other suitable compressible material. In some embodiments, the body portion 50 and the extension tube portion 60 are selectively connectable, for example, by adhesive, friction-fit, snap-fit, molding, and/or any suitable mechanical arrangement. The lumen 70 extends between leading and trailing end portions of each section 42, 44 and may have, for example, substantially circular or D-shaped cross-sections.

The body portion 50 includes an outer surface 52, which may be curvilinear or have curvilinear portions, and an inner surface 54, which may be planar or have planar portions. The outer surface 52 includes a threaded segment 56 that is configured to threadably engage the threaded portion 34a of the collar 30 as will be described in greater detail below. The leading end portion of the inner surface 54 of the body portion 50 may be recessed to accommodate the septum 24 of the catheter 20 when the leading end of the body portion 50 is positioned within one of the lumens 26, 28 of catheter 20 to secure the sections 42, 44 to the trailing end portion of the catheter 20.

The extension tube portion 60 extends proximally from, and may be disposed partly within the body portion 50. A luer adapter 80, which can be formed of a substantially rigid material, is secured to a trailing end of the extension tube 60. A clamp 90 may be secured about the extension tube portion 60 of each of the first and second sections 42 and 44 distally of the luer adapter 80. The luer adapter 80 facilitates securement of the catheter 10 to a hemodialysis machine (not shown) The clamp 90 is movable between clamped and unclamped configurations about the extension tube portion 60 to control the flow of blood through the extension tube portion 60 by compressing the extension tube portion 60. When disposed in a clamped configuration, the clamp 90 prevents blood flow through the extension tube portion 60 and when disposed in an unclamped configuration, the clamp 90 permits blood flow through the extension tube portion 60.

In use, the first section 42 and the second section 44 of the extension tube assembly 40 are adjacent each other so that the inner surfaces 54 of the first and second sections 42, 44 are opposite one another. In this position, the threaded segment 56 of the first section 42 and the threaded segment 56 of the second section 44 may be aligned or substantially aligned to define an annular threaded arrangement circumscribing or substantially circumscribing the body portions 50 of the first and second sections 42, 44. In this orientation, the leading ends of the body portions 50 of the first and second sections 42, 44 may be positioned within the respective first and second lumens 26, 28 of the catheter 20. The body portions 50 of the first and second sections 42, 44 may be independently or collectively positioned within the first and second lumens 26, 28 of the catheter 20 to position the first and second lumens 26, 28 of the catheter 20 in fluid communication with the lumens 70 defined through the respective first and second sections 42, 44.

The collar 30 may be translated from a distal position to a proximal position relative to the catheter 20, as discussed above. When moved proximally, to a position adjacent the extension tube assembly 40, the threaded portion 34a of the collar 30 threadably engages the threaded segments 56 of the first and second sections 42, 44 of the extension tube assembly 40 to secure the first and second sections 42, 44 of the extension tube assembly 40 to the trailing end portion of the catheter 20. Notably, the collar 30 is threaded proximally about the extension tube assembly 40 until suitably tightened in a manner sufficient to secure each of the first and second sections 42, 44 to the catheter 20.

More specifically, when collar 30 is secured to threaded segments 56 of sections 42 and 44 of extension tube assembly 40, sections 42 and 44 are drawn toward each other to compress catheter 20 between sections 42 and 44 and secure catheter 20 to extension tube assembly 40. When one or both of the first and second sections 42, 44 of extension tube assembly 40 require replacement, the clinician unthreads the collar 30 distally relative to the catheter 20 so that either or both sections 42, 44 may be removed from a respective lumen 26, 28 of catheter 20 and replaced. Upon repositioning sections 42 and/or 44 within a respective lumen 26, 28 of catheter 20, the collar 30 may then once again be threaded proximally about the extension tube assembly 40, as discussed above, to secure the first and second sections 42, 44 to the catheter 20. Each section 42 or 44 may be individually replaceable independently of the other section.

Referring now to FIG. 4, an extension tube assembly 300 is includes a first section 310 and a second section 320. Similar to the first and second sections 42, 44 of the extension tube assembly 40 (FIGS. 1-3), the first and second sections 310, 320 define a lumen 70 therethrough and include an extension tube portion 60, a luer adapter 80, and a clamp 90.

The first section 310 includes a first body portion 312 having an inner surface 312a and an outer surface 312b. A projection 312c is a first mating feature that extends from the inner surface 312a of the first body portion 312. The second section 320 includes a second body portion 322 having an inner surface 322a and an outer surface 322b. The inner surface 322a of the second body portion 322 defines a slot 322c, which is a second mating feature. The slot 322c receives the projection 312c of the first section 310 to facilitate the relative alignment and/or securement of the first and second sections 310, 320 to each other.

Referring now to FIG. 5, an extension tube assembly 400 includes a first section 410 and a second section 420. Similar to the first and second sections 42, 44 of the extension tube assembly 40 (FIGS. 1-3), the first and second sections 410, 420 define a lumen 70 therethrough and include an extension tube portion 60, a luer adapter 80, and a clamp 90.

The first section 410 includes a first body portion 412 having an inner surface 412a and an outer surface 412b. A first mating surface 412c is a first mating feature supported on the inner surface 412a of the first body portion 412. The second section 420 includes a second body portion 422 having an inner surface 422a and an outer surface 422b. The inner surface 422a of the second body portion 422 supports a second mating surface 422c, which is a second mating feature. The second mating surface 422c mates with the first mating surface 412c of the first section 410 to facilitate the relative alignment and/or securement of the first and second sections 410, 420 to each other. The first and second mating surfaces 412c, 422c may be formed of any of various different mating materials including magnetic material, adhesive material, and combinations thereof.

Figure 6A:
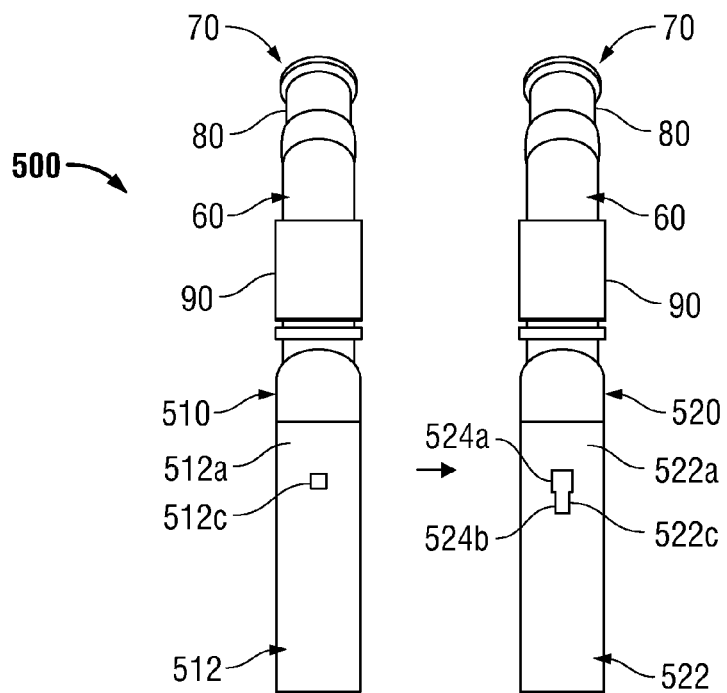
FIG. 6A is a side view of first and second sections of an extension tube assembly of a catheter assembly.
Figure 6B:
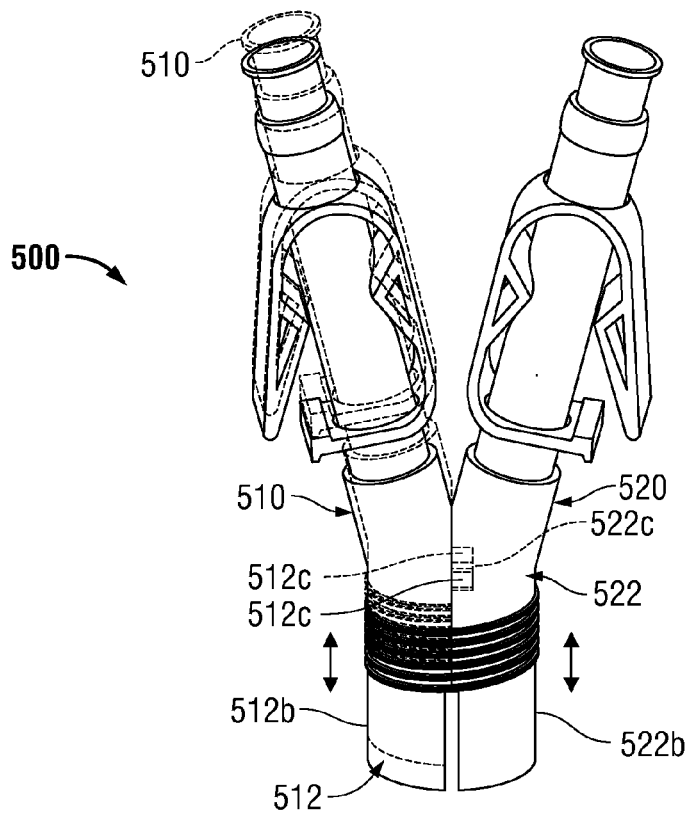
FIG. 6B is a front perspective view of the extension tube assembly of FIG. 6A.

With reference to FIGS. 6A-6B, an extension tube assembly 500 includes a first section 510 and a second section 520. Similar to the first and second sections 42, 44 of the extension tube assembly 40, the first and second sections 510, 520 define a lumen 70 therethrough and include an extension tube portion 60, a luer adapter 80, and a clamp 90.

The first section 510 includes a first body portion 512 having an inner surface 512a and an outer surface 512b. A first mating feature, namely a detent 512c, is supported on the inner surface 512a of the first body portion 512. The second section 520 includes a second body portion 522 having an inner surface 522a and an outer surface 522b. The inner surface 522a of the second body portion 522 defines a second mating feature, namely a detent slot 522c. The detent slot 522c receives the detent 512c of the first section 510 to facilitate the relative alignment and/or securement of the first and second sections 510, 520 to each other. The detent slot 522c includes a top section 524a and a bottom section 524b. As shown in FIG. 6B, the detent 512c of the first section 510 is inserted into one of sections 524a, 524b of the detent slot 522c so that relative sliding movement between the first and second sections 510, 520 will position the detent 512c of the first section 510 in the other section of the detent slot 522c. One of the top and bottom sections 524a, 524b of the detent slot 522c may be narrower than the other section to facilitate a secure interconnection between the first and second sections 510, 520. As shown in FIG. 6A, for example, the bottom section 524b is narrower than the top section 524a so that movement of the detent 512c from the top section 524a into the bottom section 524b will secure the first and second sections 510, 520 to each other.

Persons skilled in the art will understand that the structures and methods specifically described herein and illustrated in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Accordingly, the subject matter of the present disclosure is not to be limited by what has been particularly shown and described.

What is claimed is:

1. A catheter assembly, comprising:
   a catheter including a leading end portion and a trailing end portion;
   a collar supported on the trailing end portion of the catheter; and
   an extension tube assembly including a first section and a second section, each section being independent of the other section, and each section including a substantially rigid body portion and a compressible extension tube portion, the body portion of each of the first and second sections being independently engageable with the trailing end portion of the catheter, and wherein the collar is engageable with the first and second sections of the extension tube assembly to secure the extension tube assembly to the trailing end portion of the catheter.

2. The catheter assembly of claim 1, wherein the collar is threaded, the body portion of the first section of the extension tube assembly includes a first threaded segment, and the body portion of the second section of the extension tube assembly includes a second threaded segment, each of the first and second threaded segments being threadably engageable with the collar.

3. The catheter assembly of claim 2, wherein when the body portions of the first and second sections of the extension tube assembly are disposed adjacent each other, the first threaded segment of the body portion of the first section and the second threaded segment of the body portion of the second section are simultaneously threadably engageable with the collar.

4. The catheter assembly of claim 2, wherein the first threaded segment of the body portion of the first section and the second threaded segment of the body portion of the second section together define an annular threaded arrangement circumscribing the body portions of the first and second sections.

5. The catheter assembly of claim 4, wherein the first threaded segment and the second threaded segment of the respective body portions of the first and second sections define the annular threaded arrangement when the first and second threaded segments are axially aligned along a longitudinal axis defined through the extension tube assembly.

6. The catheter assembly of claim 3, wherein at least one of the first and second sections of the extension tube assembly includes a mating feature that axially aligns the first section with the second section.

7. The catheter assembly of claim 6, wherein the first section has a first mating feature including at least one slot defined in the first body portion and the second section has a second mating feature including at least one detent extending from the second body portion, the at least one detent being positionable within the at least one slot to align the first threaded segment of the body portion of the first section with the second threaded segment of the body portion of the second section.

8. The catheter assembly of claim 6, wherein the mating feature includes at least one of an adhesive material, a magnetic material, or combinations thereof.

9. The catheter assembly of claim 1, wherein the catheter defines a first lumen and a second lumen and, when the body portions of the first and second sections of the extension tube assembly are engaged with the trailing end portion of the catheter, the first lumen is in fluid communication with the extension tube portion of the first section of the extension tube assembly and the second lumen is in fluid communication with the extension tube portion of the second section of the extension tube assembly.

10. The catheter assembly of claim 1, wherein the body portions of the first and second sections each include a planar surface, each planar surface disposed opposite the planar surface of the other section when the body portions of the first and second sections are engaged with the trailing end portion of the catheter.

11. The catheter assembly of claim 1, wherein the collar is rotatably disposed about the trailing end portion of the catheter relative to the extension tube assembly for threaded engagement of the collar with the body portions of the first and second sections of the extension tube assembly to secure the extension tube assembly to the trailing end position of the catheter.

12. An extension tube assembly for attachment to a catheter, comprising:
    a first section including a first body portion and a first extension tube portion, the first body portion securable to a trailing end portion of a catheter, the first extension tube portion securable to a medical device; and
    a second section including a second body portion and a second extension tube portion, the second body portion securable, independently of the first body portion, to the trailing end portion of the catheter, the second extension tube portion securable to the medical device.

13. The extension tube assembly of claim 12, wherein the first body portion of the first section includes a first threaded segment and the second body portion of the second section includes a second threaded segment, the first and second body portions together defining an annular threaded arrangement when the first and second threaded segments are disposed adjacent each other.

14. The extension tube assembly of claim 13, wherein the annular threaded arrangement of the first and second body portions is threadably engageable with a collar supported on the catheter for simultaneously securing the first and second body portions to the catheter.

15. The extension tube assembly of claim 12, wherein at least one of the first and second sections includes a mating feature that axially aligns the first section with the second section.

16. The extension tube assembly of claim 15, wherein the first section has a first mating feature including at least one slot defined in the first body portion and the second section has a second mating feature including at least one detent extending from the second body portion, the at least one detent positionable within the at least one slot to axially align the first body portion with the second body portion.

17. The extension tube assembly of claim 16, wherein the mating feature includes at least one of an adhesive material, a magnetic material, or combinations thereof.

18. The extension tube assembly of claim 12, wherein the first body portion and the second body portion each include a planar surface, each planar surface disposed opposite the other planar surface when the first and second body portions are engaged with the trailing end of the catheter.

\* \* \* \* \*